United States Patent [19]

Takeshita et al.

[11] 3,936,478

[45] Feb. 3, 1976

[54] PROCESS FOR THE PREPARATION OF DESMOSTEROL DERIVATIVES

[75] Inventors: Toru Takeshita, Hino; Sachio Ishimoto, Tokyo, both of Japan

[73] Assignee: Teijin Limited, Osaka, Japan

[22] Filed: June 19, 1974

[21] Appl. No.: 480,823

[30] Foreign Application Priority Data
June 20, 1973 Japan.............................. 48-68657
July 3, 1973 Japan.............................. 48-74367

[52] U.S. Cl. .......................................... 260/397.2
[51] Int. Cl.² .......................................... C07J 9/00
[58] Field of Search ...................... 260/397.5, 397.2

[56] References Cited
UNITED STATES PATENTS
3,846,455  11/1974  Ikekawa et al................... 260/397.2

*Primary Examiner*—Elbert L. Roberts
*Attorney, Agent, or Firm*—Sherman & Shalloway

[57] ABSTRACT

A process for the preparation of desmosterol of which the hydroxyl group at the 3-position is protected, or bis-form derivatives thereof in high purity and with high yields, which comprises reacting 24-hydroxycholesterol of which the hydroxyl group at the 3-position is protected, or bis-form derivatives thereof, with A. phosphorus pentoxide or acid potassium sulfate, or
B. phosphorus oxychloride, thionyl chloride, or sulfonyl chlorides, in the presence of tertiary amine.

10 Claims, No Drawings

PROCESS FOR THE PREPARATION OF DESMOSTEROL DERIVATIVES

This invention relates to a process for the preparation of desmosterol derivatives. More particularly the invention relates to a process comprising dehydration of 24-hydroxycholesterol of which the hydroxyl group at the 3-position is protected, or bis-form derivatives thereof, as can be expressed by the formula (1) below, to thereby produce desmosterol of which the hydroxyl groups at the 3-position is protected or the bis-form derivatives thereof, expressed by the formula (2) below:

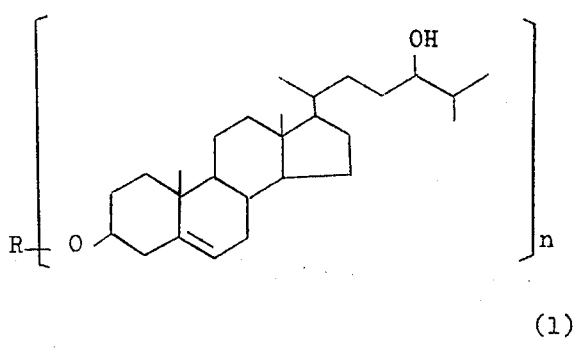

(1)

in which
R stands for a monovalent or divalent protective group, and
n is 1 or 2;

↓ dehydration reaction

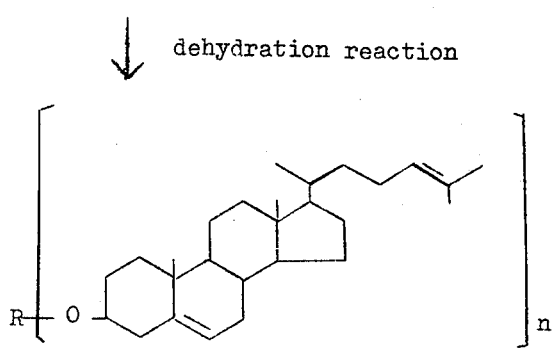

(2)

in which R and n have the same definitions as given as to the formula (1).

Desmosterol of the formula (3) below

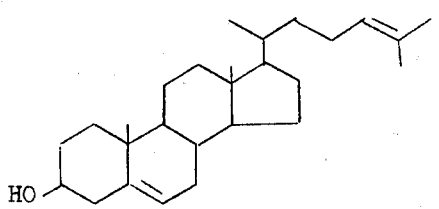

(3)

and the derivatives thereof are valuable compounds as the intermediates of biologically active steroids or of active forms of Vitamin $D_3$ such as 1.25-dihydroxycholecalciferol, 24,25-dihydroxycholecalciferol, and 25-hydroxycholecalciferol.

It is known to make desmosterol or the derivatives thereof from 3$\beta$-acetoxy-5-cholenic acid, by synthesizing 3$\beta$-acetoxy-5-cholenaldehyde from the starting material via the acid chloride of 3$\beta$-acetoxy-5-cholenic acid and ethyl 3$\beta$-acetoxythiol-5-cholenate, and then subjecting the aldehyde to Wittig reaction with isopropyl bromide, to thereby form desmostrol 3-acetate (refer to *J. Am. Chem. Soc.*, 79, p. 6473). Desmosterol 3-acetate is also known to be formable from methyl 3$\beta$-hydroxy-5-cholenate, through six stages (see U.S. Pat. No. 3,152,152), or from methyl 3$\beta$-acetoxychol-5-ene-24-carboxylate, through 5 stages [see *J. C. S. Perkin I* (1973), 2423 - 2425].

However, all of those known methods use as the starting material 3$\beta$-hydroxycholenic acid of the formula (4) below,

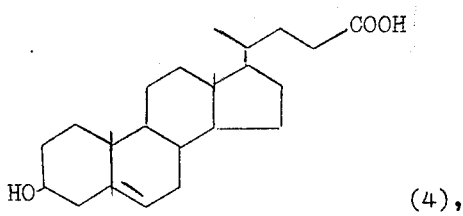

(4), which is very expensive. They also involve many and complex steps before the object product is obtained only with insufficient yields. Thus, they are hardly satisfactory for industrial practice.

It has also been proposed to use 25-ketonorcholesterol of the formula (5) below

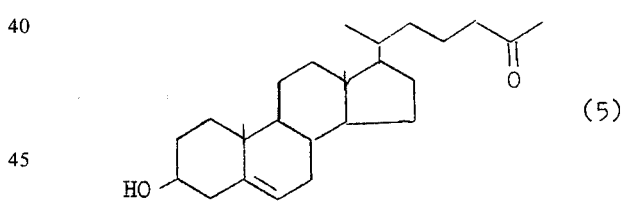

(5)

as the starting material, which is converted to 25-hydroxycholesterol by Grignard reaction, and then dehydrated in the presence of sulfuric acid or phosphorus oxychloride to provide desmosterol or an ester thereof (see *J. Org. Chem.* 23, p. 459, and *J. Lipid Research*, 8, p. 152). This method however again has such deficiencies as that the starting 25-ketonorcholesterol is expensive and that the yield of dehydration reaction is low. Particularly when phosphorus oxychloride is used in the reaction, substantial amounts of 25-dehydrocholesterol 3-acetate is produced as a by-product. Thus, the method is not industrially advantageous.

Accordingly, an object of the present invention is to provide a novel process for making desmosterol derivatives through a reaction requiring less steps, with high yield.

Another object of the invention is to provide a process for making desmosterol derivatives with high yield, from 24-hydroxycholesterol of which the hydroxyl group at the 3-position is protected, or from bis-form derivatives thereof, through a simple dehydration reaction.

Still many other objects and advantages of the invention will become apparent from reading the following descriptions.

The foregoing objects and advantages of the invention are accomplished by reacting 24-hydroxycholesterol of which the hydroxyl group at the 3-position is protected or bis-form derivatives thereof, of the formula (1) below,

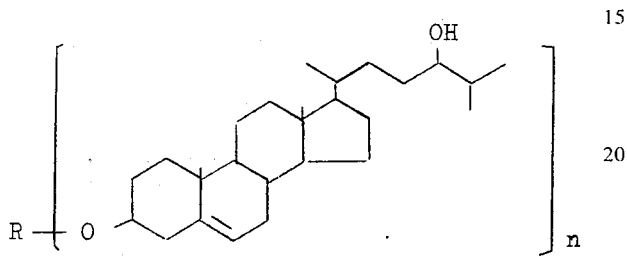

(1)

in which
R stands for a monovalent or divalent protective group, and
$n$ is 1 or 2;
with
A. phosphorus pentoxide or potassium hydrogen-sulfate, or
B. phosphorus oxychloride, thionyl chloride, or sulfonyl chlorides, in the presence of tertiary amine, to thereby produce desmosterol or bis-form derivatives thereof of which the hydroxyl group at the 3-position is protected, of the formula (2) below:

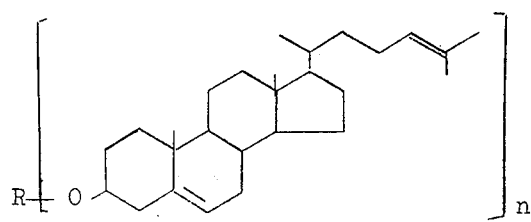

(2)

in which the definitions of R an $n$ are the same as given for formula (1) above.

[STARTING COMPOUNDS]

Referring to the definitions given as to the formula (1) denoting the starting compounds to be employed in this invention, when $n$ is 1, R is a monovalent protective group, and when $n$ is 2, obviously R is a divalent group.

Consequently, the formula (1) covers the two groups of compounds expressed by the formulae (1-a) and (1-b) below:

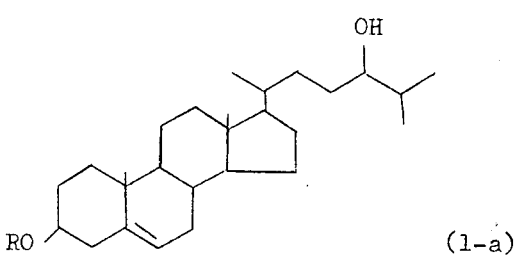

(1-a)

in which R is a monovalent protective group, and

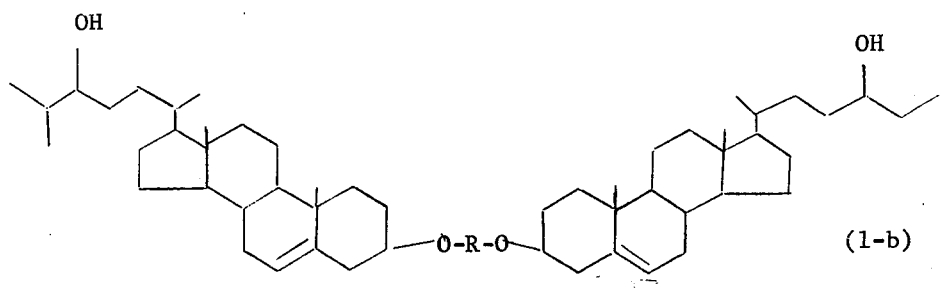

(1-b)

in which R is a divalent protective group.

The formula (1-a) covers the cases wherein the $n$ is 1 referring to formula (1), and formula (1-b), those wherein the $n$ is 2.

The R in the formula (1) may be any protective group, so far as it can be transformed to hydroxyl group by any suitable means such as hydrolysis, reduction, or the like, after the compounds of formula (2) are formed according to the invention, without destroying or changing the structures of the compounds of formula (2) or derivatives thereof.

The R in the formula (1-a) denotes such monovalent protective groups, and that in formula (1-b) covers such divalent protective groups.

Preferred examples of such protective groups R include the following:

A. substituted or unsubstituted, saturated or unsaturated, and monovalent or divalent, hydrocarbon residues of 1 to 12 carbon atoms, and B. substituted or unsubstituted, and saturated or unsaturated carboxylic acid residues of 1 to 12 carbon atoms, i.e., the acyl groups derived from such carboxylic acids.

When R is a hydrocarbon residue within the group (A) above the hydroxyl group at the 3-position of 24- hydroxycholesterol is protected by forming an ether. Whereas, when the R is a member of the group (B) the hydroxyl group is protected by the carboxylic acid.

The protective groups will be further explained with more specific examples. The hydrocarbon residues of group (A) can be roughly divided into two large subgroups of aliphatic hydrocarbon residues and aromatic hydrocarbon residues. In either case the hydrogen atom or atoms of the residues may be substituted with inert substituent groups such as halogen atom, alkoxy, nitro, acyl, carboxyl, ester of carboxyl, alkyl (for aliphatic hydrocarbon residues only), and aromatic groups (for aromatic hydrocarbon residues only). Furthermore, with the aliphatic hydrocarbon residues, the methylene groups thereof may be substituted with oxygen atoms, forming ethers.

Specific examples of the aliphatic hydrocarbon residues include alkyl groups such as methyl, ethyl, n-propyl, n-butyl, n-pentyl, n-hexyl, heptyl, octyl, nonyl, dodecyl, iso-propyl, iso-butyl, sec-butyl, t-butyl, iso-pentyl, neopentyl, ter-pentyl, iso-hexyl, cyclopentyl, and cyclohexyl; alkenyl groups such as allyl, butenyl, iso-propenyl, hexenyl, snf cyclohexenyl; alkylene groups such as methylene, ethylene, trimethylene, tetramethylene, pentamethylene, and hexamethylene; aliphatic hydrocarbon residues substituted with monovalent inert substituent groups such as chloromethyl, β-chloroethyl, benzyl, nitrobenzyl, cinnamyl, chlorobenzyl, and phenethyl; and aliphatic hydrocarbon residues in which the methylene group is substituted with oxygen atom, such as tetrahydropyranyl and methoxymethyl.

Of the above-named examples, particularly the alkyl groups of 1 to 6 carbon atoms and benzyl are preferred.

Also the specific examples of aromatic hydrocarbon residues include aryl groups such as phenyl and naphthyl; arylene groups such as phenylene; and substituted aromatic hydrocarbon residues such as tolyl, ethylphenyl, cumenyl, chlorophenyl, and methoxyphenyl.

The carboxylic acid residues of the group (B) can be further divided into two large subgroups of aliphatic carboxylic acid residues and aromatic carboxylic acid residues, in which the hydrogen atom or atoms may be substituted with monovalent, inert substituent groups such as halogen atom, alkoxy, nitro, acyl, carboxyl, ester of the carboxyl, alkyl (aromatic carboxylic acid residues only), aromatic groups (aliphatic carboxylic acid residues only).

Specific examples of such carboxylic acid residues include: saturated aliphatic monocarboxylic acid residues such as acetyl, propanoyl, butanoyl, pentanoyl, hexanoyl, capronyl, capryryl, laurayl, cyclohexanoyl, and cyclopentanoyl; unsaturated aliphatic monocarboxylic acid residues such as acrylyl, methacrylyl, α-ethylacrylyl, β-methylcrotonyl, crotonyl, heptanoyl, and algeloyl; substituted aliphatic carboxylic acid residues such as fluoroacetyl, chloroacetyl, bromoacetyl, dichloroacetyl, trichloroacetyl, α-chloropropanoyl, α-bromocapronyl, phenylacetyl, phenylpropanoyl, cinnamoyl, naphthylacetyl, m-nitrocinamoyl, p-nitrophenylacetyl, nitrophenylpropanoyl, acetoacetyl, levulinoyl, carboxyacetyl, methoxycarboxyacetyl, ω-carboxypropylacetyl, carboxyphenylacetyl, and carboxynaphthylacetyl; saturated and unsaturated dicarboxylic acid residues such as oxalyl, malonyl, succinyl, glutaryl, adipoyl, sebacyl, maleyl, fumaryl, glutaconoyl, and dihydromuconoyl; and substituted aliphatic dicarboxylic acid residues such as chloromalonyl, bromomalonyl, dichloromalonyl, chlorosuccinyl, and bromosuccinyl.

Also as the specific examples of aromatic carboxylic acid residues, the following may be named: aromatic monocarboxylic acid residues such as benzoyl and naphthoyl; aromatic carboxylic acid residues substituted with monovalent, inert substituent groups such as ethylbenzoyl, toluyl, trimethylbenzoyl, methylnaphthoyl, fluorobenzoyl, chlorobenzoyl, dichlorobenzoyl, chloronaphthoyl, nitrobenzoyl, dinitrobenzoyl, methoxybenzoyl, carboxybenzoyl, 2,4-dicarboxylbenzoyl, carboxynaphthoyl, and methoxycarbonylbenzoyl; aromatic dicarboxylic acid residues such a phthaloyl, isophthaloyl, terephthaloyl, and naphtholoyl, and aromatic dicarboxylic acid residues substituted with monovalent, inert substituent groups such as chlorophthaloyl, chloroterephthaloyl, dichloroterephthaloyl, and nitroterephthaloyl.

The 24-hydroxychlolesterol derivatives used as a starting material in the process of this invention can be synthesized easily in high yields from fucosterol occurring in great quantities in seaweeds belonging to brown algae and contained in great quantities in industrial wastes from the sodium alginate-producing industry. One example of the method of synthesis involves oxidizing a fucosterol derivative with ozone in a customary manner to form a 24-ketocholesterol derivative easily, and treating this 24-ketocholesterol derivative with a suitable reducing agent to form the desired 24-hydroxycholesterol derivative in high yields. [Dehydrating agent and dehydration reaction conditions]

According to the invention, the compounds of the foregoing formula (1), i.e., those of the formula (1-a) or (1-b), are contacted with the dehydrating agent hereinbelow described, as closely as possible to cause the dehydrating reaction.

We discovered the following dehydrating agents to be effective for the present invention:

A-1. phosphorus pentoxide
A-2 acid potassium sulfate
B-1 phosphorus oxychloride
B-2 thionyl chloride, and
B-3 sulfonyl chlorides We also found that known dehydrating agents other than the above five types are substantially ineffective.

Of the above-named, particularly the dehydrating agents of A-1, A-2, B-1, and B-2 are favorably used, phosphorus pentoxide (A-1) being the most advantageous.

The starting material employed in this invention, i.e., 24-hydroxycholesterol of which the hydroxyl group at the 3-position is protected, or the bis-form derivatives thereof, expressed by the formula (1), cannot be converted to the desmosterol derivatives of the formula (2) intended by the invention, with known dehydrating agents such as, for example, sulfuric acid, polyphosphoric acid, and the like. It is indeed surprising, therefore, that the same starting material is convertible to the desmosterol derivatives with high yields, when the above-specified five types of dehydrating agents, particularly preferably phosphorus pentoxide, are used. The specified dehydrating agents are used at the ratio of 0.5 to 100 molar times, preferably from 1 to 50 molar times, the starting compound of the formula (1) with advantage.

When phosphorus pentoxide (A-1) or acid potassium sulfate (A-2) is used as the dehydrating agent, the dehydrating reaction is advantageously performed in an inert solvent, at the temperatures ranging from −10°C to 150°C., perferably from −5°C. to 130°C. Particularly when phosphorus pentoxide is used, the optimum reaction temperature ranges from −5°C. to 50°C. Thus the dehydrating reaction can be completed normally within 5 minutes to 20 hours. The reaction time is variable within said range depending on such factors as the reaction temperature and type and quantity of the dehydrating agent.

If any one of
(B-1) phosphorus oxychloride,
(B-2) thionyl chloride, or
(B-3) sulfonyl chlorides
is used as the dehydrating agent, the dehydrating reaction should be performed in the presence of tertiary amine as the acid acceptor.

As the sulfonyl chlorides, those covered by the formula below, $$R'SO_2Cl$$

in which R' is a monovalent organic group, preferably an aromatic or aliphatic group of 1 to 10 carbon atoms, can be used with favorable results. More specifically, particularly methanosulfonyl chloride, toluenesulfonyl chloride, and benzene sulfonyl chloride, for example, are preferred.

Also as the tertiary amines, for example, aliphatic tertiary amines such as triethylamine, tri-n-propylamine, tri-n-butylamine, tri-isobutylamine, dimethylethylamine, 1,4-diazabicyclo[2,2,2]octane, and 1,5-diazabicyclo[4,3,0]-5-nonene; aromatic amines such as dimethylaniline, diethylaniline, and triphenylamine; pyridines; picolines; lutidines; collidines; quinolines; and heterocyclic compounds such as pyridazine and pyrimidine can be used, particularly triethylamine, tri-n-propylamine, pyridines, lutidines, and collidines being preferred.

Of the above-named tertiary amines, those which are liquid at the temperatures at which the dehydrating reaction of the invention is performed, function also as the inert solvent, besides their action as the acid acceptor.

The dehydrating reaction using the dehydrating agent (B-1), (B-2), or (B-3) is performed in the presence of 0.5 to 100 mols, preferably 1 to 50 mols, of the dehydrating agent per mol of the starting compound of the formula (1) at −10°C to 180°C., preferably from 0°C. to 150°C., with advantage. The reaction is normally completed within 5 minutes to 30 hours.

The dehydrating reaction of the invention is advantageously performed in an inert solvent. Whereas, when phosphorus oxychloride (B-1), thionyl chloride (B-2), or sulfonyl chlorides (B-3) is used as the dehydrating agent, the reaction should be performed in the presence of a tertiary amine as aforesaid. When the tertiary amine is liquid at the reaction temperature, the whole or a part of the inert solvent may be substituted with the tertiary amine.

The type of the inert solvent is not critical, so far as it is a liquid medium which does not interfere with the dehydrating reaction intended by the present invention, and can dissolve the starting compound of the formula (1), the dehydrating agent, and if used, the tertiary amine.

As such inert solvent, for example, aliphatic hydrocarbons such as petroleum ether, ligroine, hexane, pentane, cyclohexane, decaline, and methylcyclohexane; aromatic hydrocarbons such as benzene, toluene, xylene, and ethylbenzene; halogenated hydrocarbons such as carbon tetrachloride, tetrachloroethane, and tetrachloroethylene; ethers such as ethyl ether, tetrahydrofurane, and dioxane; and esters such as ethyl acetate and butyl acetate, can be used with preference.

In a preferred embodiment of the invention, therefore, 24-hydroxycholesterol 3-acetate of the formula (1-c) below,

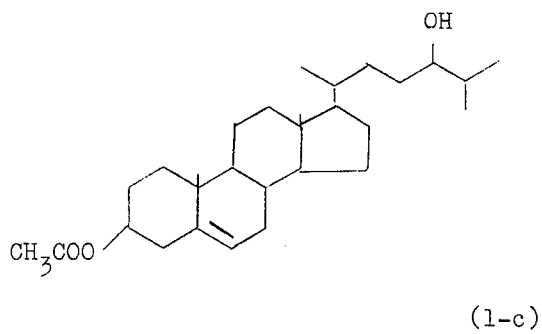

(1-c)

for example, is reacted with phosphorus pentoxide in an inert solvent, at the temperatures within the range of −5°C. to 50°C., to form through a simple single-stage reaction desmosterol 3-acetate of the formula (2-c) below,

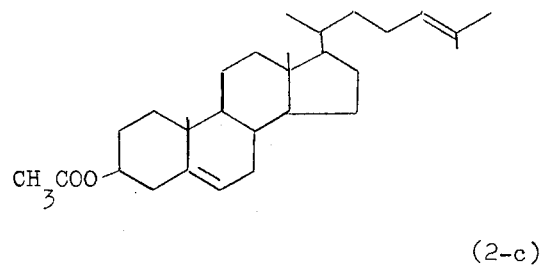

(2-c)

with a high yield.

[The product, and its separation and refining]

The above-described dehydrating reaction produces the desmosterol with its 3-positioned hydroxyl group protected as expressed by the formula (2-a),

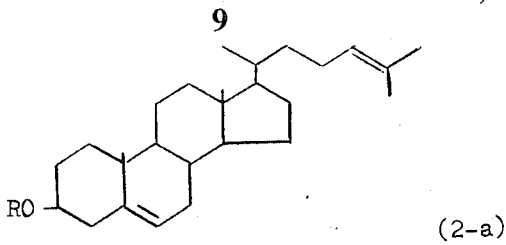

(2-a)

in which R denotes a monovalent protective group, when 24-hydroxycholesterol of which the hydroxyl group at the 3-position is protected, as shown by the formula (1-a), is used as the starting material. Whereas, if the bis-form derivatives of the compound of formula (1-a), i.e., the compound of the formula (1-b), is used as the starting material, the corresponding bis-form derivative of desmosterol of which the hydroxyl group at the 3-position is protected, of the formula (2-b) below, is obtained.

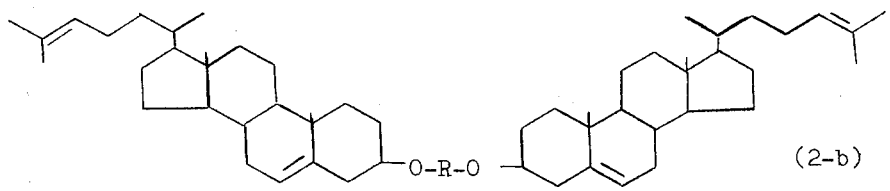

(2-b)

in which R denotes a divalent protective group.

After completion of the reaction, if the reaction mixture containing the formed object product of the formula (2-a) or (2-b) also contains the dehydrating agent or decomposition product thereof in the form of solid, the mixture is subjected to an optional solid-liquid separation means such as filtration, centrifugation, sedimentation, or decantation. Or, if the dehydrating agent dissolves in the reaction mixture, the dehydrating agent or decomposition products thereof can be separated by such steps as, for example, adding water to the reaction mixture to thereby extract the dehydrating agent or the decomposition products into the water, and separating the aqueous phase from the inert solvent phase containing the object product.

Obviously, the above solid-liquid separation may be effected by the aqueous extraction, or the solid-liquid separation means may be practiced in combination with the aqueous extraction.

The object product then can be separated from the reaction mixture from which the dehydrating agent or the decomposition products thereof had been removed, by distilling off the inert solvent, or, if necessary, by first suitably concentrating the system and then recrystallizing the product from other suitable solvents, or by subjecting the system to column chromatography. Through such means, the object product separated may also be refined.

Again according to the invention, the reaction mixture containing the so formed desmosterol or bis-form derivatives thereof of which the hydroxyl group at the 3-position is protected, as expressed by the formula (2-a) or (2-b) may be hydrolyzed or reduced either directly or after the removal of the dehydrating agent or decomposition product thereof, under suitable conditions. The protective group is thereby eliminated and the object product can be converted to desmosterol. For example, if the hydroxyl group at the 3-position is protected by a carboxylic acid residue, the product can be transformed to desmosterol by the hydrolysis under the conditions normally employed for that of esters, i.e., the hydrolysis using an acid or alkali. In a more specific embodiment, a caustic potash-methanol solution containing a sufficient amount of caustic potash is added to the reaction mixture containing desmosterol with its 3-positioned hydroxyl group protected by a carboxylic acid residue, and the system is hydrolyzed at a temperature within the range of room temperature to 60°C., if necessary in the presence of an inert solvent such as benzene. Thus free desmosterol can be obtained.

Or, the carboxyl compounds may be reduced by a suitable metal hydride such as excessive lithium aluminium tetra-hydride, to free desmosterol.

If the 3-positioned hydroxyl group is protected by a hydrocarbon residue, such desmosterol derivatives can be easily converted to desmosterol by a treatment with hydrochloric acid, provided the hydrocarbon residue is such that can be easily eliminated with acid, e.g., tetrahydropyranyl, methoxymethyl, or the like. Other hydrocarbon residues serving as the protective groups can be eliminated, by treating the desmosterol derivatives with hydrogen iodide, aluminium bromide, boron tribromide, or the like.

The desmosterol product again can be easily separated from the above reaction mixture and refined, by such means as the recrystallization or column chromatography.

According to the invention, therefore, the desmosterol derivatives of the formula (2-a) or (2-b) may also be separated as desmosterol.

The utility of the specified five types of compounds (A-1), (A-2), (B-1), (B-2), and (B-3), as dehydrating agent per se is known. However, of the numerous compounds known as functioning as dehydrating agents, only the specified five types of compounds show unique reactivity in the dehydrating reaction of 24-hydroxycholesterol and bis-form derivatives thereof with their hydroxyl groups at 3-positions protected, and form the desmosterol derivatives through simple operation, furthermore with high yields. The reaction for making desmosterol derivatives using such dehydrating agents is entirely novel.

Thus, according to the invention desmosterol of which the hydroxyl group at the 3-position is protected (2-a), or bis-form derivatives thereof (2-b), or desmosterol, can be formed with high yields.

The invention is particularly characteristic in that the desmosterol derivatives containing a double bond at 24-position as indicated by the formula (2-a) or (2-b) can be selectively formed.

Our studies confirmed that when 25-hydroxycholesterol derivatives are dehydrated, for example, with phosphorus oxychloride, the compound having the double bond at 25-position and desmosterol derivatives (containing the double bond at 24-position) are formed at the ratio of approximately 1:1. In the face of that fact, it is indeed surprising that upon dehydration of 24-hydroxycholesterol according to the subject process, the desmosterol derivatives are selectively formed.

As will be demonstrated by the below described Control, dehydration of 25-hydroxycholesterol with sulfuric acid yields desmosterol derivatives, but it is extremely difficult to form the object desmosterol derivatives by dehydrating the 24-hydroxycholesterol derivatives of the formula (1), which is used as the starting material in the subject process, with sulfuric acid.

Furthermore, according to the invention the formation of olefins by elimination of the group RO-bonded at the 3-position of A ring hardly takes place.

As so far described, high-purity desmosterol derivatives or desmosterol converted therefrom can be formed and recovered through simple reaction procedures, with high yields.

Hereinafter the invention will be explained with reference to the working examples, which are given for the sole purpose of facilitating the understanding of the invention, and should never be construed to limit the scope of the invention.

EXAMPLE 1

350 Milligrams of phosphorus pentoxide was added to 24 ml of benzene, and while the system was maintained at 10°C., 440 mg of 24-hydroxycholesterol 3-acetate was added under stirring, during 3 minutes. The stirring was continued for 35 minutes more, and then 30 ml of water was added to the reaction mixture to separate the benzene phase. The benzene phase was washed with water, and dried with sodium sulfate. Then the benzene was distilled off under a reduced pressure, leaving 430 mg of a white solid.

The product was separated and refined by means of column chromatography, using the column filled with 200-mesh silica gel (elution being effected with benzene-n-hexane mixed solvent). Thus 360 mg (yield = 85%) of the product having the physical properties as indicated below was obtained.

Melting point, 93° – 94°C.
$[\alpha]_D^{19} = -42.7°$ ($c = -0.48$, CHCl$_3$)
IR($\nu_{max}$, cm$^{-1}$, KBr);
 1,730, 1,370, 1,250, 800
NMR (CDCl$_3$, δ (ppm));
 0.67 (3H, s, C-18-H,s),
 1.01 (3H, s, C-19-H,s),
 1.60 (3H, s, C-26-H,s or C-27-H,s),
 1.69 (3H, s, C-26-H,s or C-27-H,s),
 2.01 (3H, s, CH$_3$CO-),
 4.63 (1H, b, C-3-H),
 5.08 (1H, t, J=6.5H$_z$, C-24-H),
 5.35 (1H, m, C-6-H)
s: singlet, b: broad, t: triplet, m: multiplet,
Mass Spectra (m/e);
 366 (M-CH$_3$COOH), 351, 253, 145, 93, 69, From the above data, the product obtained was identified to be desmosterol 3-acetate.

Incidentally, according to the disclosures of *J. Org. Chem.*, 23, 459 (1958), desmosterol 3-acetate had the melting point of 92.5° – 93°C., and $[\alpha]_D^{25}$ equals –40.6 ($c = 0.9$, CHCl$_3$).

EXAMPLES 2 – 11

24-Hydroxycholesterol 3-acetate and phosphorus pentoxide were reacted in a manner similar to Example 1, in the reaction solvent and at the temperature which are both indicated in Table 1, for the times also indicated in the same Table.

Except for Example 10, the reaction products were separated through the steps of adding water to the reaction system to separate the organic phase, washing the organic phase with water and drying with sodium sulfate, and distilling off the organic solvent under a reduced pressure. In Example 10, water and ethyl were added instead of water alone, to separate the ether phase.

The product separated in each run was first eluted with a mixed solvent of benzene and n-hexane, through a chromato-column filled with 200-mesh silica gel. Thus the product (I) was obtained. Further, elution with a mixed solvent of benzene and ethyl acetate yielded the product (II).

The product (I) was identified to be desmosterol 3-acetate from the melting point, $[\alpha]_D^{19}$, IR, NMR, and mass spectra.

Also the product (II) was identified to be desmosterol, because the results of gas chromatography (1.5% OV-1 on chromosorb WHP) corresponded with those of desmosterol, and the product showed the melting point and NMR as given below.

Melting point: 120° – 121°C.
NMR (CDCl$_3$, δ (ppm));
 0.67 (3H, s, C-18-H,s),
 1.00 (3H, s, C-19-H,s),
 1.60 (3H, s, C-26-H,s or C-27-H,s),
 1.68 (3H, s, C-26-H,s or C-27-H,s),
 3.50 (1H, b, C-3-H),
 5.08 (1H, t, J=6.5H$_z$, C-24-H),
 5.30 (1H, m, C-6-H)

According to *J. Org. Chem.* 23 459 (1958), desmosterol has the melting point at 120.5° – 121°C.

The results of the reaction were as shown in Table 1.

Table 1

| Example No. | 24-hydroxy cholesterol 3-acetate (mg) | Solvent kind (ml) | $P_2O_5$ (mg) | Reaction temp. (°C.) | Reaction time (min.) | Yield Desmosterol 3-acetate (Product I) (mg) | (%) | Desmosterol (Product II) (mg) | (%) |
|---|---|---|---|---|---|---|---|---|---|
| 2 | 300 | Methylene chloride (20) | 310 | −5 | 50 | 210 | 73 | — | — |
| 3 | 300 | Benzene (20) | 280 | 25 | 40 | 150 | 52 | 3 | 1.2 |
| 4 | 300 | Benzene (30) | 150 | 50 | 20 | 138 | 48 | 7.8 | 3.0 |
| 5 | 150 | Toluene (18) | 70 | 90 | 20 | 63 | 44 | 3.6 | 2.8 |
| 6 | 440 | Methylene chloride (25) | 400 | 5 | 20 | 330 | 78 | — | — |
| 7 | 300 | Cyclohexane (40) | 300 | 10 | 40 | 190 | 66 | — | — |
| 8 | 300 | Tetrachloroethylene (28) | 260 | 5 | 50 | 204 | 71 | — | — |
| 9 | 300 | Chlorobenzene (25) | 300 | 5 | 40 | 181 | 63 | — | — |
| 10 | 100 | Tetrahydrofuran (10) | 600 | 60 | 320 | 41 | 43 | — | — |
| 11 | 100 | Ethylene acetate (10) | 600 | 60 | 240 | 43 | 45 | — | — |

EXAMPLE 12

A solution composed of 30 ml of toluene, 440 mg of 24-hydroxycholesterol 3-acetate, and 3.0 g of acid potassium sulfate, was stirred for 3 hours at 110°C. After completion of the reaction, 40 ml of water was added to the reaction mixture, to separate the toluene phase, which was subsequently treated similarly to Example 1. Thus 300 mg of the refined product was recovered, with the yield of 70%, which showed the physical properties identical with those of the desmosterol 3-acetate obtained in Example 1.

EXAMPLES 13 – 18

24-Hydroxycholesterol 3-acetate and acid potassium sulfate were reacted in the reaction solvent at the temperature and for the time each specified in Table 2.

Excepting Example 18, the reaction products were separated by the steps of adding water to the reaction system to separate the organic phase, washing the organic phase with water and drying with sodium sulfate, and distilling off the organic solvent under a reduced pressure. In Example 18, the water as the extraction agent was replaced by water and ethyl ether, and the ether phase was separated. The refining of the product was effected in the identical manner with that of Example 1.

The results were as shown also in Table 2.

EXAMPLE 19

A mixture of 460 mg of 24-hydroxycholesterol 3-propionate and 30 ml of tetrachloroethylene was maintained at 110°C.; 2.0 g of acid potassium sulfate was added to the mixture under stirring. After stirring for 4 more hours 30 ml of water was added to separate the tetrachloroethylene phase, which was treated in a similar manner to Example 1 to yield 300 mg of the refined product. The yield was 67%.

The product showed NMR as follows:
NMR (CDCl$_3$, δ (ppm));
0.67 (3H, s, C-18-H,s),
1.02 (3H, s, C-19-H,s),
1.60 (3H, s, C-26-Hs,s, or C-27-H,s),
1.68 (3H, s, C-26-H,s or C-27-H,s),
4.62 (1H, b, C-3-H),
5.07 (1H, t, J=6.5H$_z$, C-24-H),
5.35 (1H, m, C-6-H)

When the product was reduced with lithium aluminium tetrahydride in ethyl ether at room temperature, a product having the melting point (119° – 120°C.) and NMR identical with those of the desmosterol formed in Examples 3 – 5 was obtained. From the qualitative analyses data, the product of this Example was identified to be desmosterol 3-propionate.

Table 2

| Example No. | 24-Hydroxy cholesterol 3-acetate (mg) | Solvent (ml) | Acid potassium sulfate (g) | Reaction temp. (°C.) | Reaction time (hr) | Yield desmosterol 3-acetate (mg) | (%) |
|---|---|---|---|---|---|---|---|
| 13 | 300 | Benzene (30) | 3 | 60 | 12 | 138 | 48 |
| 14 | 150 | Toluene (18) | 1.5 | 80 | 10 | 82 | 57 |
| 15 | 150 | o-Xylene (20) | 1.5 | 144 | 3 | 95 | 66 |
| 16 | 300 | Tetrachloroethylene (30) | 3 | 110 | 3 | 178 | 62 |
| 17 | 300 | Chlorobenzene (30) | 3 | 105 | 4 | 156 | 52 |
| 18 | 100 | Dioxane (15) | 1.5 | 100 | 25 | 39 | 41 |

EXAMPLE 20

A solution formed of 30 ml of benzene and 250 mg of 24-hydroxycholesterol 3-benzoate was maintained at 5°C. under stirring; 200 mg of phosphorus pentoxide was added to the solution. After stirring for 30 minutes, the system was treated similarly to Example 1. Thus 242 mg of a light yellow solid was recovered from the benzene phase, which was refined through a chromato-column filled with silica gel (eluting agent: benzene-n-hexane mixed solvent) to yield 162 mg of the product having NMR as follows. The yield was 67%.

NMR (CDCl$_3$, δ (ppm));
  0.68 (3H, s, C-18-H,s),
  1.05 (3H, s. C-19-H,s),
  1.60 (3H, s, C-26-H,s, or C-27-H,s),
  1.68 (3H, s, C-26-H,s or C-27-H,s),
  4.70 (1H, b, C-3-H),
  5.00 (1H, m, C-24-H),
  5.37 (1H, m, C-6-H),
  7.49 (3H, m, benzoate-ortho-H,s),
  8.02 (2H, m, benzoate-meta and para-H,s), The product was hydrolyzed in a methanol solution of caustic potash at 60°C. for an hour. Thus a product having the melting point (120°C.) and NMR identical with those of the desmosterol obtained in Examples 3 – 5 was obtained. From those data, the product of this Example was identified to be desmosterol 3-benzoate.

EXAMPLE 21

A solution formed of 20 ml of benzene and 100 mg of 24-hydroxycholesterol 3-caprylate was maintained at 10°C. under stirring, to which solution 100 mg of phosphorus pentoxide was added. After stirring for 30 minutes, the system was treated similarly to Example 1. Thus 96 mg of a light yellow, oily substance was recovered from the benzene phase, which was then refined through a chromato-column filled with silica gel (eluting agent: a mixed solvent of benzene and n-hexane) to give 56 mg of the refined product. The yield was 58%.

The product showed NMR data as follows:
NMR (CDCl$_3$, δ (ppm));
  0.67 (3H, s, C-18-H,s),
  1.02 (3H, s, C-19-H,s),
  1.60 (3H, s, C-26-H,s or C-27-H,s),
  1.68 (3H, s C-26-H,s or C-27-H,s),
  4.63 (1H, b, C-3-H),
  5.08 (1H, t, J=6.5 H$_z$, C-24-H),
  5.35 (1H, m, C-6-H).

The product was hydrolyzed under the identical conditions with those employed for the hydrolysis of the product of Example 20, to form a product of which melting point (119° – 120°C.) and NMR corresponded to those of desmosterol.

From those results, the product was identified to be desmosterol 3-caprylate.

EXAMPLE 22

A solution formed of 30 ml of benzene and 100 mg of bis(24-hydroxycholesterol) 3,3'-terephthalate was maintained at 10°C. under stirring, and 70 mg of phosphorus pentoxide was added to the solution. The system was stirred for 40 minutes more, and then treated similarly to Example 1. From the benzene phase, 97 mg of a white solid was recovered, which was refined through a chromato-column filled with silica gel (eluting agent: benzene) to yield 53 mg of a product. The yield was 55%.

The product showed the NMR analysis results as follows:
NMR (CDCl$_3$, δ (ppm));
  0.68 (6H, s, C-18-H,s),
  1.04 (6H, s, C-19-H,s),
  1.60 (6H, s, C-26-H,s or C-27-H,s),
  1.67 (6H, s, C-26-H,s or C-27-H,s),
  4.70 (2H, b, C-3-H),
  5.10 (2H, b, C-24-H),
  5.38 (2H, C-6-H),
  8.03 (4H, s, benzene ring-H,s), The same product was hydrolyzed in a methanol-benzene solution of caustic potash at 60°C. for 1.5 hours, to form a product of which melting point (118° – 120°C.) and NMR perfectly corresponded to those of the desmosterol obtained in Examples 3 through 5.

From those results the product of this Example was identified to be bis(desmosterol)3,3'-terephthalate.

EXAMPLE 23

A solution formed of 15 ml of toluene, 150 mg of 24-hydroxycholesterol 3-benzoate, and 1.5 g of acid potassium sulfate was maintained at 110°C., under stirring for 3 hours. After completion of the reaction, the system was treated similarly to Example 12, and 150 mg of a light yellow solid was recovered from the toluene phase. The same solid was refined by means of column chromatography using a column filled with silica gel (eluting agent: benzene-n-hexane mixed solvent) to yield 75 mg of desmosterol 3-benzoate showing the same NMR spectra with those of the product of Example 20. The yield was 52%.

EXAMPLE 24

To 25 ml of n-hexane, 0.40 g of phosphorus pentoxide was added, and maintained at 0°C. under stirring. Then 420 mg of 3-methoxy-24-hydroxy-cholest-5-ene was added to the solution, consuming 1.5 minutes, followed by stirring for 30 minutes more. Thereafter 25 ml of water and 25 ml of ethyl ether were added to separate the organic phase. By distilling n-hexane and ether off from the organic phase under a reduced pressure, 400 mg of a white, crystalline product was obtained. The solid was separated and refined by means of a chromato-column filled with silica gel (eluting agent: benzene-n-hexane mixed solvent) to recover 250 mg of a refined product. The yield was 59%.

The product had the NMR as follows, and from the data is identified to be 3-methoxycholesta-5,24-diene.
NMR (CDCl$_3$, δ(ppm));
  0.67 (3H, s, C-18-H,s),
  1.01 (3H, s, C-19-H,s),
  1.60 (3H, s, C-26-H,s or C-27-H,s),
  1.69 (3H, s, C-26-H,s or C-27-H,s),
  3.00 (1H, b, C-3-H),
  3.31 (3H, s, CH$_3$O-),
  5.04 (1H, t, J=6.5H$_z$, C-24-H),
  5.34 (1H, m, C-6-H),

EXAMPLE 25

To a solution formed of 20 ml of methylene chloride and 150 mg of 3β-n-butoxy-24-hydroxycholest-5-ene maintained at 10°C., 150 mg of phosphorus pentoxide was added. The system was stirred for subsequent 30 minutes, and treated similarly to Example 1. Thus 142 mg of a white solid was recovered from the methylene chloride phase. The solid was refined by column chromatography (absorbent: silica gel, eluting agent:

benzene-n-hexane mixed solvent) to yield 79 mg of the purified product. The yield was 55%.

The product had the NMR as follows, and from the data is identified to be 3β-n-butoxy-cholesta-5,24-diene.

NMR (CDCl$_3$, δ(ppm));
0.65 (3H, s, C-18-H,s),
0.98 (3H, s, C-19-H,s),
1.58 (3H, s, C-26-H,s or C-27-H,s),
1.62 (3H, s, C-26-H,s, or C-27-H,s),
3.00 (1H, b, C-3-H),
3.37 (2H, m, —CH$_2$—O—),
5.04 (1H, m, C-24-H),
5.30 (1H, m, C-6-H)

EXAMPLE 26

To a solution formed of 50 mg of 24-hydroxycholest-5-en-3β-(2'-tetrahydropyranyl)-ether and 10 ml of benzene maintained at 24°C., 150 mg of phosphorus pentoxide was added. The system was stirred for 60 minutes more, and after completion of the reaction extracted with 1% aqueous sodium carbonate solution and ethyl ether. The separated organic phase was washed thoroughly with water, and dried with anhydrous sodium sulfate. Then the benzene and ethyl ether were distilled off under a reduced pressure.

The residue was passed through a chromato-column filled with silica gel which had been deactivated with water, and eluted first with a benzene-n-hexane mixed solvent to give 14.4 mg of further product (III). The yield was 30%. Then the elution with a benzene-ethyl acetate mixed solvent, to give 5 mg of the product (IV). The yield was 13%.

The NMR of the product (III) was as follows:
NMR (CDCl$_3$, δ(ppm));
0.67 (3H, s, C-18-H,s),
1.00 (3H, s, C-19-H,s),
1.60 (3H, s, C-26-H,s or C-27-H,s),
1.69 (3H, s, C-26-H,s or C-27-H,s),
3.10 – 3.90 (4H, b, C-3-H and the proton at 2 position of pyranyl group)
5.08 (1H, m, C-24-HO),
5.35 (1H, m, C-6-H), When the product (III) was treated with hydrochloric acid, a product showing the same melting point (119°– 120°C.) and NMR with those of the desmosterol obtained in Examples 3 through 5 was obtained.

Based on those results, the product (III) was identified to be cholesta-5,24-diene-3β-(2'-tetrahydropyranyl) ether.

Also the product (IV) had the melting point and NMR corresponding to those of desmosterol which was the hydrochloric acid-decomposed product of above product (III), and from that fact was identified to be desmosterol.

EXAMPLE 27

A solution formed of 15 ml of toluene, 50 mg of 3β-n-butoxy-24-hydroxycholest-5-ene, and 700 mg of acid potassium sulfate was maintained at 110°C. under stirring for 2 hours. After completion of the reaction, the system was treated similarly to Example 12, and 47 mg of a solid was recovered from the toluene phase. By refining the solid through a silica gel-filled chromato-column (eluting agent: benzene-n-hexane mixed solvent), 23 mg of a product was obtained. The yield was 48%. Because the product showed the NMR perfectly identical with that of the product of Example 25, it was identified to be 3β-(n-butoxy)-cholesta-5,24-diene.

EXAMPLE 28

440 Milligrams of 24-hydroxycholesterol 3-acetate was dissolved in 11 ml of pyridine, and while the solution was maintained at 22°C., 1.1 ml of phosphorus oxychloride was dropped slowly thereinto, followed by stirring for an hour. Thereafter the reaction solution was poured into ice water, and extracted with 50 ml of ether.

The ether phase was washed with diluted hydrochloric acid, further repeatedly washed with water, and finally dried with sodium sulfate. Distilling the ether off under a reduced pressure yielded 420 mg of a white, crystalline product.

The solid was separated and refined by means of a silica gel-filled chromato-column (eluting agent: benzene-n-hexane mixed solvent), to yield 260 mg of the refined product. The yield was 61%.

The product had the melting point at 92°–93°C., and its NMR well corresponded to that of the product of Example 1. Thus the product was identified to be desmosterol 3-acetate.

EXAMPLES 29 – 36

24-Hydroxycholesterol 3-acetate was reacted with phosphorus oxychloride or thionyl chloride in the presence of tertiary amine. The amounts of the reactants, type of the tertiary amine, and the reaction temperature and time employed in each run were as shown in Table 3. The reaction mixtures were treated similarly to Example 28, and the products were separated and refined.

The results were as given also in Table 3.

All the products were identified to be desmosterol 3-acetate, from the melting points and NMR analyses data.

Table 3

| Sample No. | 24-Hydroxy cholesterol 3-acetate (mg) | POCl$_3$ or SOCl$_2$ (ml) | t-amines (ml) | Reaction temp. (°C.) | Reaction time (hr) | Yield desmosterol 3-acetate (mg) | (%) |
|---|---|---|---|---|---|---|---|
| 29 | 200 | POCl$_3$ (0.3) | pyridine (5) | 50 | 6 | 109 | 57 |
| 30 | 200 | POCl$_3$ (0.3) | pyridine (5) | 98 | 2 | 105 | 55 |
| 31 | 440 | SOCl$_2$ (1.1) | pyridine (11) | 15 | 2.5 | 230 | 55 |
| 32 | 100 | SOCl$_2$ (0.25) | pyridine (2.5) | 50 | 3 | 48 | 50 |
| 33 | 100 | SOCl$_2$ (0.20) | pyridine (2.8) | 76 | 2 | 50 | 52 |
| 34 | 220 | POCl$_3$ (1.0) | trichylamine (10) | 0–18 (gradually rising) | 20 | 140 | 66 |

Table 3-continued

| Sample No. | 24-Hydroxy cholesterol 3-acetate (mg) | POCl₃ or SOCl₂ (ml) | t-amines (ml) | Reaction temp. (°C.) | Reaction time (hr) | Yield desmosterol 3-acetate (mg) | (%) |
|---|---|---|---|---|---|---|---|
| 35 | 440 | POCl₃ (0.6) | s-collidine (13) | 22 | 5 | 279 | 66 |
| 36 | 100 | SOCl₂ (0.28) | α-picoline (3) | 20 | 3 | 47 | 49 |

EXAMPLE 37

250 Milligrams of 24-hydroxycholesterol 3-benzoate was dissolved in 15 ml of pyridine, and maintained at 20°C. Into the solution 1.0 ml of phosphorus oxychloride was added dropwise, followed by stirring for 20 hours. Thereafter the reaction liquid was poured into water, and extracted with a benzene-ether mixed solvent.

The organic phase was separated, washed with water, dried with sodium sulfate, and the organic solvent was distilled off.

The residue was refined similarly to Example 1, and 150 mg of a product showing the NMR well corresponding to that of the product of Example 20 (desmosterol 3-benzoate) was obtained. The yield was 62%. When the product was hydrolyzed with a methanol solution of caustic potash at 60°C. for an hour, the product had the melting point (119° – 120°C.) and NMR identical with those of desmosterol.

From the foregoing results, the product of this Example was identified to be desmosterol 3-benzoate.

EXAMPLE 38

100 Milligrams of 3β-n-butoxy-24-hydroxycholest-5-ene was dissolved in 3 ml of pyridine. While the solution was maintained at 20°C., 0.30 ml of thionyl chloride was added thereto, followed by stirring for 3 hours. The reaction mixture was treated similarly to Example 28, and 94 mg of a white solid was refined by means of column chromatography using silica gel and a benzene-n-hexane mixed solvent. Thus 50 mg of a product was obtained with the yield of 52%.

From the results of NMR analysis, the product was identified to be 3β-(n-butoxy)-cholesta-5,24-diene.

EXAMPLE 39

58 Milligrams of 24-hydroxycholest-5-en-3β-(2'-tetrahydropyranyl)-ether was dissolved in 1.5 ml of pyridine, and while the solution was maintained in 18°C., 0.1 ml of phosphorus oxychloride was slowly added, followed by stirring for 2 hours. The reaction mixture was treated similarly to Example 28, and 49 mg of a light yellow solid was separated from the ethyl ether phase.

The solid was refined by column chromatography using the silica gel which had been deactivated with water and a mixed solvent of benzene and n-hexane as the eluting agent. Thus 23 mg of a product having the NMR corresponding to that of cholesta-5,24-dien-3β-(2'-tetrahydropyranyl)-ether was obtained. The yield was 42%.

Treatment of the product with hydrochloric acid yielded a material which had the melting point (118.5° – 120°C.) and NMR corresponding to those of desmosterol.

From those results, the product of this Example was identified to be cholesta-5,24-dien-3β-(2'-tetrahydropyranyl)-ether.

EXAMPLE 40

To a solution formed from 0.44 g of 24-hydroxycholesterol 3-acetate and 13 ml of pyridine, 0.50 g of p-toluenesulfonyl chloride was added at room temperature. After reaction for 3 hours at 110°C., the reaction liquid was poured into ice water, and extracted with 100 ml of ether. The ether phase was washed with 5% aqueous sodium carbonate solution and 1N hydrochloric acid, and then repeatedly with water. Then the ether phase was treated similarly to Example 28, to separate 193 mg of a product with the yield of 46%. The product had the melting point at 93.5° – 94°C., and its NMR well corresponded to that of desmosterol 3-acetate.

EXAMPLES 41 – 45

24-Hydroxycholesterol 3-acetate was reacted with various sulfonyl chlorides in the presence of tert.-amines. The amounts of the reactants, type of t.-amine, and reaction temperature and time employed for each run were as shown in Table 4. The reaction mixtures were treated similarly to Example 40, and the products were separated and refined.

The results were as shown in Table 4. All the products were identified to be desmosterol 3-acetate, from their melting points and NMR analyses data.

Table 4

| Example No. | 24-Hydroxy cholesterol 3-acetate (mg) | Sulfonyl chlorides (mg) | t-amine (ml) | Reaction temp. (°C.) | Reaction time (hr.) | Yield desmosterol 3-acetate (mg) | (%) |
|---|---|---|---|---|---|---|---|
| 41 | 150 | p-Toluene sulfonyl chloride (240) | pyridine (5) | 40–50 | 18 | 56 | 39 |
| 42 | 100 | p-Toluene sulfonyl chloride (150) | pyridine (4) | 83 | 18 | 38 | 40 |
| 43 | 100 | p-Toluene sulfonyl chloride (120) | s-collidine (4) | 158 | 3 | 41 | 43 |
| 44 | 150 | Methan sulfonyl chloride (400) | pyridine DMF 4 ml | 110 | 3.5 | 72 | 50 |
| 45 | 100 | Benzene | pyridine | 110 | 4 | 44 | 46 |

Table 4-continued

| Example No. | 24-Hydroxy cholesterol 3-acetate (mg) | Sulfonyl chlorides (mg) | t-amine (ml) | Reaction temp. (°C.) | Reaction time (hr.) | Yield desmosterol 3-acetate (mg) (%) |
| --- | --- | --- | --- | --- | --- | --- |
| | | sulfonyl chloride (110) | (4) | | | |

EXAMPLE 46

120 Milligrams of 24-hydroxycholesterol-3-benzoate was dissolved in 6 ml of pyridine, and while the solution was maintained at 110°C., 150 mg of p-toluenesulfonyl chloride was added thereto, followed by stirring for 3 hours. The reaction mixture was treated similarly to Example 40, passed through a chromato-column filled with silica gel, and refined as extracted by the mixed solvent of benzene and n-hexane. Thus 51 mg of a product was obtained, with the yield of 44%.

The product showed NMR identical with that of the product of Example 20, and when it was hydrolyzed with a caustic potash-methanol solution at 60°C. for an hour, had the melting point (118.5° − 120°C.) and NMR identical with those of desmosterol.

From those results, the product of this Examples was identified to be desmosterol 3-benzoate.

EXAMPLE 47

43 Milligrams of 3β-n-butoxy-24-hydroxycholest-5-ene was dissolved in 2 ml of pyridine, and to the solution which was maintained at 110°C., 60 mg of p-toluenesulfonyl chloride was added and reacted for 6 hours. The reaction mixture was treated similarly to Example 40, separated and refined through a chromato-column filled with silica gel, a benzene-n-hexane mixed solvent being used for the elution. Thus 16 mg of a product showing the NMR identical with that of 3β-n-butoxy-cholesta-5,24-diene was obtained. The yield was 38%.

EXAMPLE 48

130 Milligrams of phosphorus pentoxide was added to 10 ml of benzene, and maintained at −5°C. under stirring. Then 200 mg of 24-hydroxycholesterol 3-acetate was added thereto, and the system was stirred for further 40 minutes at that temperature and reacted. Thereafter the solid and benzene phase were separated by decantation. To the benzene phase 10 ml of methanol and 10 ml of 2N-caustic potash-methanol solution were added to effect the hydrolyzing reaction for an hour while refluxing methanol. After the reaction ethyl ether and water were added to the system, and the ethyl ether phase was separated, which was subsequently washed with 1N-hydrochloric acid, then repeatedly with water, and dried with anhydrous Glauber's salt. The ethyl ether was distilled off under a reduced pressure, leaving 168 mg of a light yellow solid. The solid was separated and refined through a chromato-column filled with silica gel, and eluted with a mixed solvent of benzene and ethyl acetate. Thus 131 mg of desmosterol having the same properties with those of the product of Examples 3 – 5 was obtained. The yield was 76%.

CONTROL

A sulfuric acid-dioxane system which has been reported to be effective for the synthesis of desmosterol from 25-hydroxycholesterol 3-acetate (cf. *J. Org. Chem.*, 23 456 (1958)) was applied to the reaction of 24-hydroxycholesterol 3-acetate.

To 6 ml of 12% sulfuric acid-dioxane mixture (% by weight), 25 mg of 24-hydroxycholesterol 3-acetate was added, and stirred for 2 days at room temperature.

Thereafter the reaction mixture was poured into water, and extracted with ether. The extract was acetylated in an acetic anhydride-pyridine system and analyzed. Whereupon it was found that the object desmosterol 3-acetate was obtained with the yield not higher than 5%.

When the above reaction was performed at 50°C. for 30 minutes, a large amount of side-products was obtained, and the yield of desmosterol 3-acetate was only 10%.

We claim:

1. A process for the preparation of desmosterol of which the hydroxyl group at the 3-position is protected, or bis-form derivatives thereof, of the formula (2) below:

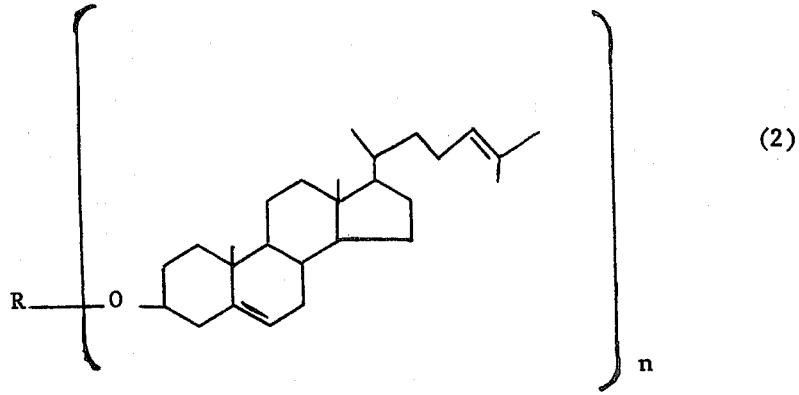

in which R denotes respectively a monovalent or divalent protective group which is convertible into a hydroxyl group through hydrolysis or reduction, and $n$ is respectively 1 or 2, which comprises reacting 24-hydroxycholesterol of which the hydroxyl group at the 3-position is protected, or bis-form derivatives thereof, of the formula (1) below:

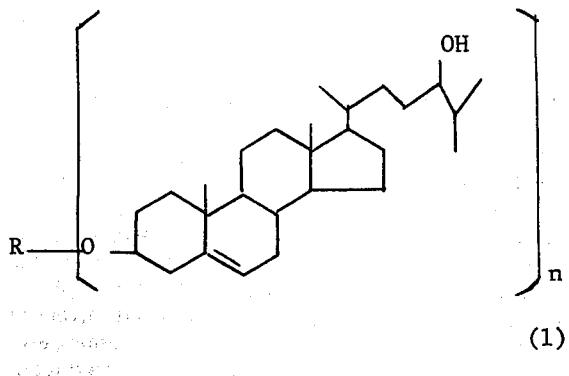

(1)

in which R and n have the same definitions as given for formula (2), with a dehydrating agent selected from the group consisting of
(A)(1) phosphorus pentoxide, (A)(2) acid potassium sulfate,
(B)(1) phosphorus oxychloride, (B)(2) thionyl chloride, and (B)(3) sulfonyl chlorides, with the proviso that when the dehydrating agent is (B)(1), (B)(2) or (B)(3) it is used in the presence of tertiary amine.

2. The process according to claim 1, in which the protective group R in the formula (1) or (2) is a substituted or unsubstituted, saturated or unsaturated, monovalent or divalent, hydrocarbon residue of 1 to 12 carbon atoms, or a substituted or unsubstituted, saturated or unsaturated, carboxylic acid residue of 1 to 12 carbon atoms.

3. The process for the preparation of desmosterol of which the hydroxyl group at the 3-position is protected or bis-form derivatives thereof, of the formula (2) below:

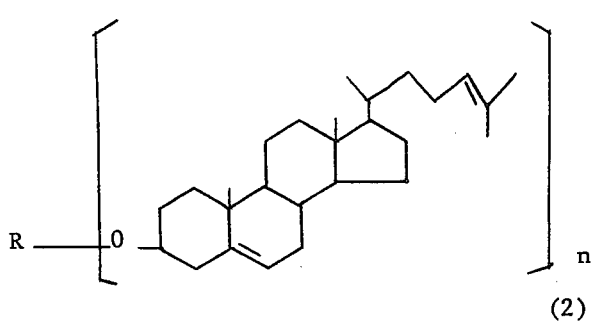

(2)

in which R denotes a monovalent or divalent protective group, and n is 1 or 2, according to claim 1, which comprises reacting 24-hydroxycholesterol of which the hydroxyl group at the 3-position is protected, or bis-form derivatives thereof, of the formula (1) below:

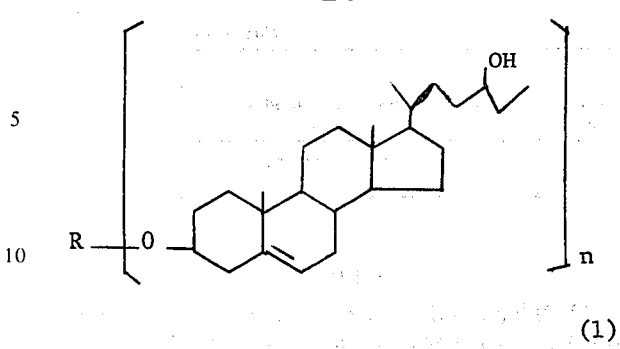

(1)

in which R and n have the same definitions as given for formula (2), with phosphorus pentoxide or acid potassium sulfate in the presence of an inert solvent, at the temperatures ranging from −10°C. to 150°C.

4. The process for the preparation of desmosterol of which the hydroxyl group at the 3-position is protected, or bis-form derivatives thereof, of the formula (2) below:

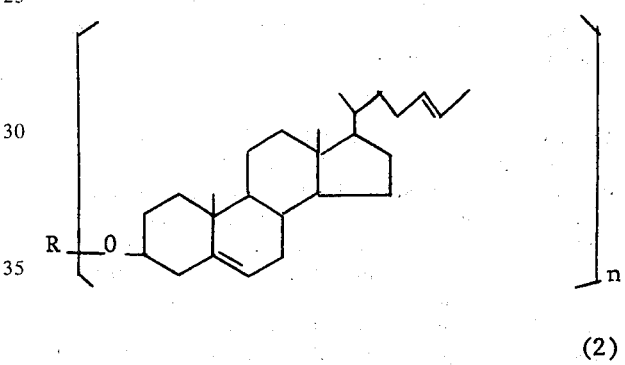

(2)

in which R denotes a monovalent or divalent protective group, and n is 1 or 2, according to claim 1, which comprises reacting 24-hydroxylcholesterol of which the hydroxyl group at the 3-position is protected, or bis-form derivatives thereof, of the formula (1) below:

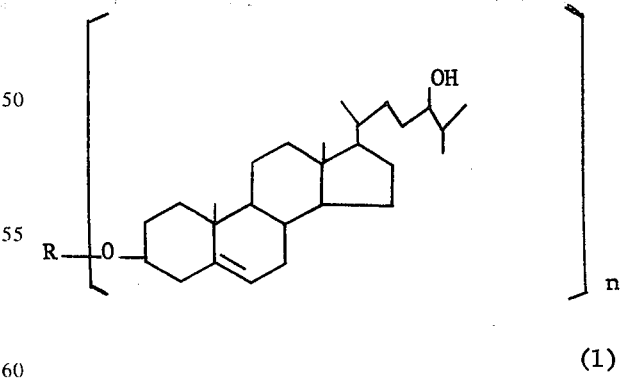

(1)

in which R and n have the same definitions as given for formula (2), with phosphorus oxychloride, thionyl chloride, or sulfonyl chloride in the presence of tertiary amine, at the temperatures ranging from 0°C. to 180°C.

5. The process for the preparation of desmosterol 3-acetate of the formula (2-c) below:

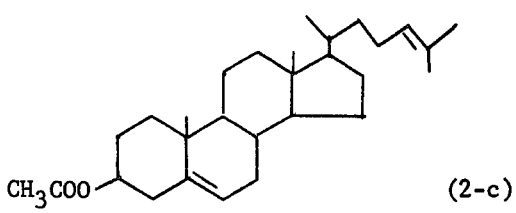

(2-c)

according to claim 1 which comprises reacting 24-hydroxycholesterol 3-acetate of the formula (1-c) below:

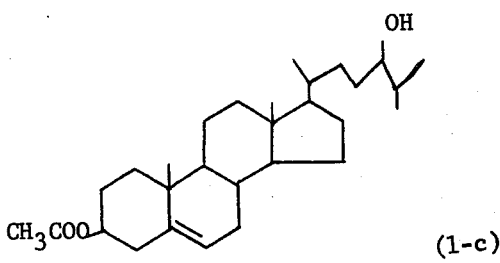

(1-c)

with phosphorus pentoxide in the presence of an inert solvent at the temperatures ranging from −5°C. to 50°C.

6. A process for the preparation of desmosterol of the formula (3) below:

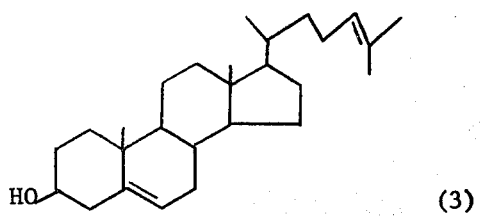

(3)

which comprises reacting 24-hydroxycholesterol of which the hydroxyl group at the 3-position is protected, or bis-form derivatives thereof, of the formula (1) below:

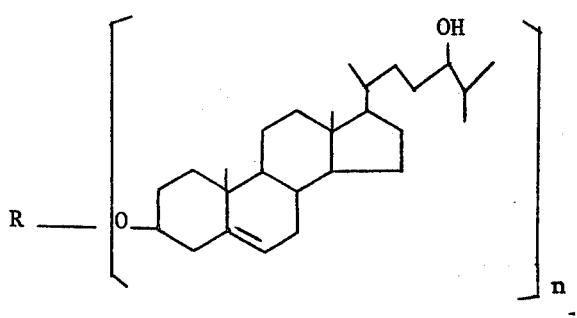

(1)

in which R denotes respectively a monovalent or divalent protective group which is convertible into a hydroxyl group through hydrolysis or reduction, and $n$ respectively is 1 or 2, with a dehydrating agent selected from the group consisting of (A)(1) phosphorus pentoxide, (A)(2) acid potassium sulfate,
(B)(1) phosphorus oxychloride, (B)(2) thionyl chloride, and (B)(3) sulfonyl chlorides, with the proviso that when the dehydrating agent is (B)(1), (B)(2) or (B)(3) it is used in the presence of tertiary amine, to form the corresponding desmosterol of which the hydroxyl group at the 3-position is protected, or bis-form derivatives thereof, of the formula (2) below:

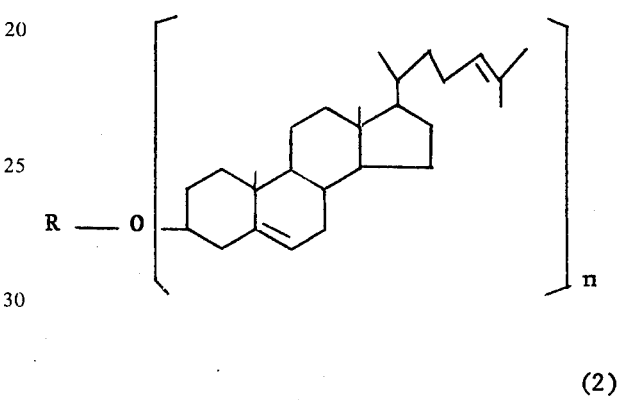

(2)

in which R and $n$ have the same definitions as given for formula (1), and hydrolyzing or reducing the same to eliminate the protective group (—R, or —R—).

7. The process of claim 1 wherein R is selected from the group consisting of saturated or unsaturated hydrocarbon residues of 1 to 12 carbon atoms which may optionally contain oxygen atom to form ether linkage and saturated or unsaturated carboxylic acid residues of 1 to 12 carbon atoms.

8. The process of claim 1 wherein said dehydrating agent is phosphorus pentoxide (A-1) and the dehydrating reaction is carried out in an inert solvent at a temperature of −5° to 50°C.

9. The process of claim 6 wherein R is selected from the group consisting of saturated or unsaturated hydrocarbon residues of 1 to 12 carbon atoms which may optionally contain oxygen atom to form ether linkage and saturated or unsaturated carboxylic acid residues of 1 to 12 carbon atoms.

10. The process of claim 6 wherein said dehydrating agent is phosphorus pentoxide (A-1) and the dehydrating reaction is carried out in an inert solvent at a temperature of −5° to 50°C.

* * * * *